US00PP29498P2

(12) United States Plant Patent
Hansen

(10) Patent No.: US PP29,498 P2
(45) Date of Patent: Jul. 10, 2018

(54) ***SALVIA* PLANT NAMED 'MIDNIGHT MODEL'**

(50) Latin Name: ***Salvia pratensis* (Linnaeus)**
Varietal Denomination: Midnight Model

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/731,781

(22) Filed: Jul. 31, 2017

(51) Int. Cl.
*A01H 5/02* (2018.01)

(52) U.S. Cl.
USPC ..... Plt./475

(58) Field of Classification Search
USPC ..... Plt./475
See application file for complete search history.

*Primary Examiner* — Annette H Para

(57) ABSTRACT

The new and distinct cultivar of perennial *Salvia* plant named 'Midnight Model' characterized by its very large, striking, strong violet flowers with dark green calyxes densely arranged in verticils, compact rounded habit with stiff, upright, branched stems, large, rugose, dark-green foliage, strong vigorous growth rate, and winter-hardy.

1 Drawing Sheet

Botanical denomination: *Salvia pratensis* (Linnaeus).
Cultivar designation: 'Midnight Model'.

BACKGROUND OF THE INVENTION

The present invention relates to a new and distinct cultivar of ornamental Sage plant hereinafter referred to by the cultivar name *Salvia* 'Midnight Model' or as the new plant. The new plant was from open pollinated seed collected by the inventor in the summer of 2013 at a wholesale perennial nursery in Zeeland, Mich., USA. The female (seed) parent 'Pink Dawn' U.S. Plant Pat. No. 26,343 and male (pollen) parent is unknown. *Salvia* 'Midnight Model' was placed in comparison trials at a the same nursery in Zeeland, Mich. in the summer of 2014 and assigned the breeder code 13-10-2 during the initial trials in 2014 and final trials in the summer of 2015 when it was approved for introduction. The plant was initially asexually propagated by basal vegetative shoot cuttings taken in 2014. The resulting plants of *Salvia* 'Midnight Model' asexually propagated at the same wholesale perennial nursery in Zeeland, Mich. have been found to be true to type and stable in successive generations.

No plants of *Veronica* 'Midnight Model' have been sold in this country, or anywhere in the world, prior to the filing of this application, nor has any disclosure of the new plant been made prior to the filing of this application with the exception of that which was disclosed or sold within one year of the filing of this application and was either derived directly or indirectly from the inventor.

SUMMARY OF THE INVENTION

Plants of *Salvia* 'Midnight Model' have not been observed under all possible environmental conditions. The phenotype may vary somewhat with variations in environment such as temperature, nutrition and light intensity, etc. without, however, any variance in genotype.

The nearest comparison cultivars are *Salvia* 'Twilight Serenade' (not patented) and *Salvia* 'Indigo' (not patented). *Salvia* 'Midnight Model' is more compact and shorter in habit, with larger flowers of more strong violet than that of the purple flowers of 'Indigo'. Compared with 'Twilight Serenade', the new plant is slightly taller and the flowers of 'Twilight Serenade' are slightly more purplish.

The following characteristics in combination distinguish *Saliva* 'Midnight Model' as a new and distinct cultivar:

1. Very large, striking, strong violet colored flowers dark green calyxes densely arranged in verticils from late spring into early summer;
2. Full mounded habit with many stiff, upright, branched flowering stems;
3. Strong, vigorous and winter-hardy growth;
4. Large, rugose, dark-green foliage.

BRIEF DESCRIPTION OF THE DRAWINGS

The photographs of the new plant demonstrate the unique traits and the overall appearance of *Salvia* 'Midnight Model'. The colors are as accurate as reasonably possible with color reproductions. Variation in ambient light spectrum, source and direction may cause the appearance of minor variation in color. The plant used in the photographs was a two-year-old plant grown in a partially shaded greenhouse at a wholesale perennial nursery in Zeeland, Mich. with supplemental water and fertilizer when needed. No plant growth regulators have been used.

DETAILED BOTANICAL DESCRIPTION

Figure 1:
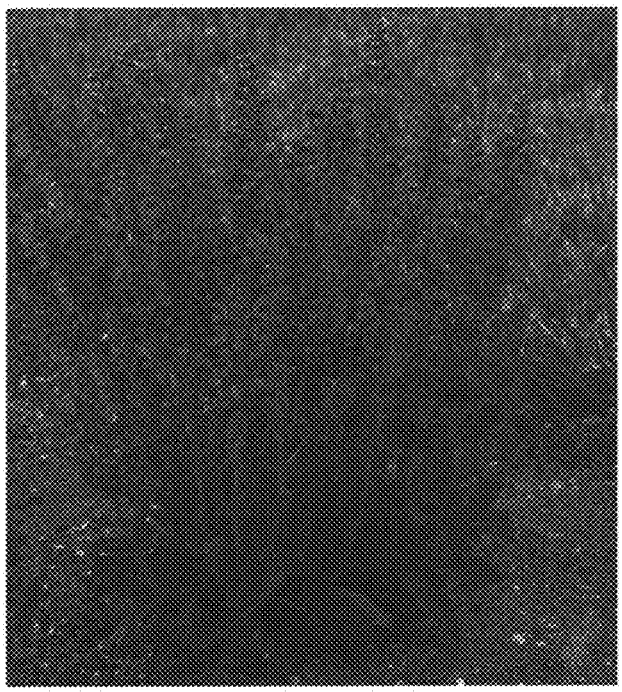
FIG. 1 shows the plant habit in full flower in a full-sun garden.
Figure 2:
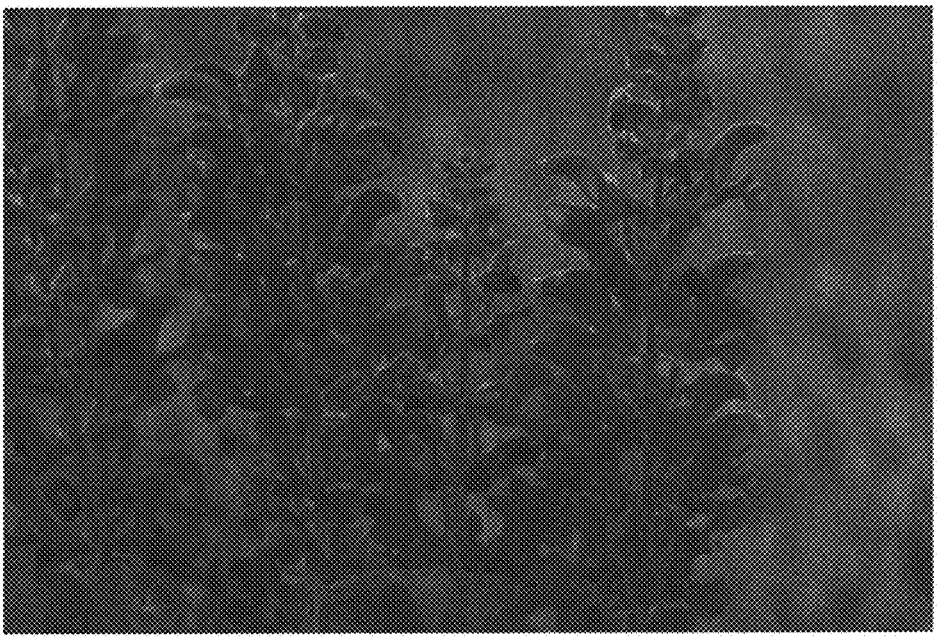
FIG. 2 shows a close-up of the flower scape with the buds, calyxes and vivid violet-blue petal color.

The following descriptions and color references except where common dictionary terms are used are based on the 2015 edition of The Royal Horticultural Society Colour Chart. *Salvia* 'Midnight Model' has not been observed under all possible environments. The phenotype may vary slightly with different growing environments such as temperature, light, fertility, soil pH, moisture and plant maturity levels, but without any change in the genotype. The following observations and size descriptions are based on two-year-old plants growing in a partially shaded greenhouse and also in a full-sun trial garden at a wholesale perennial nursery in Zeeland, Mich. Plants were given supplemental water and fertilizer but no plant growth regulators were used.

Botanical classification: *Salvia pratensis* (Linnaeus);

Parentage: Female or seed parent is 'Pink Dawn' U.S. Plant Pat. No. 26,343; unknown male or pollen parent;

Plant habit: Winter-hardy herbaceous perennial; multi-stemmed; with opposite foliage larger in basal portion and distally smaller; flowering in several tightly arranged verticils on branched upright racemes displayed above foliage; with flowering panicles about 60 cm tall and overall about 75 cm wide at the fullest point; foliage extends up the stems to about two thirds the height of plant;

Propagation: By herbaceous, basal vegetative shoot cuttings; time to produce rooted shoots about two weeks;

Growth rate: Rapid, vigorous, finishing in a 65 mm container in about 7 weeks from rooted cutting; and flowering in a two-gallon container in about 8 weeks from a one-year-old clump Root description: fine, well-branched; color dependent on age and soil type, from cream to dark tan in color;

Foliage: Opposite; simple; rugose; lanceolate; surface glabrous adaxial and puberulent to pubescent abaxial; margin crenate; acute apex and base cordate to auriculate with lobes typically overlapping only in lower leaves; blades to about 15.2 cm long and about 7.0 cm across, decreasing in size distally; average leaves about 12.0 cm long and 5.5 cm across; sage fragrance; Foliage color: young emerging leaves adaxial nearest RHS 146B, abaxial between RHS 146B and RHS 146C; mature leaves adaxial nearest RHS 139A, abaxial surface nearest RHS 137A;

Venation: Reticulate; impressed on adaxial side and costate on abaxial side; abaxial surface pubescent, adaxial puberulent;

Vein color: Emerging and mature adaxial midrib between RHS 137C and RHS 145D, main veins nearest RHS 138B and veinlets same color as surrounding tissue; abaxial midrib and main veins nearest RHS 145C, veinlets nearest RHS 145D proximally and becoming nearest RHS 138B distally;

Petiole: Concavo-convex; adaxial and abaxial surfaces pubescent; to about 7.0 cm long and 6.5 mm wide, average 5.5 cm long and 4.0 mm wide at base; pointing upwardly and outwardly;

Petiole color: Adaxial surfaces center nearest RHS 147C and margins nearest RHS 137C; abaxial center nearest RHS 147C and margins nearest RHS 147C;

Flower description: Perfect, bilabiate, verticillate with flowering generally beginning at lower verticils and advancing up the scape; with lower lip projected at about 10 to 30 degree angle above horizontal and hood petal about 45 to 60 degree angle above horizontal; self-cleaning, petals not persistent; flowering beginning late spring for about three weeks and repeating after a four week rest if initial scapes removed; average about 20 mm long, 14.0 mm tall and 9.0 mm wide at lower lip;

Flower longevity: About four days on the plant or as cut flower;

Fragrance: No fragrance detected;

Flower buds one to two days prior to anthesis: Shape is flattened laterally, rounded on top and slightly concave below, with rounded apex; pubescent; about 10.0 mm long, 7.0 mm tall and 2.0 mm wide;

Bud color: Exposed petals between RHS 94B and RHS 94C; abaxial calyx nearest RHS138A with veins nearest RHS 138A;

Petals: Bilabiate corolla with fused base; about 22.0 mm long with exserted style, 16.0 mm tall and 7.0 mm wide across lower labium;

Hood (upper) petal: Abaxial petal surface of upper hood petal puberulent distally and proximally and adaxial surface glabrous; upper hood petal fused to lower labium in basal 9.0 mm; upper hood petal and flattened side to side vertically with emarginate apex notched about 2.0 mm deep, 20.0 mm long, 5.0 mm tall and 2.0 mm wide;

Labium (lower petal): Lower labium of three lobes with two side lobes and one broad middle lobe; lower labium pubescent only on abaxial surface near center line of each lobe, glabrous adaxial and proximal and distal abaxial portion; side lobes conduplicate with outer edges folded down; acute apex and fused base; about 3.0 mm long and 2.0 mm wide unfolded; center lobe concaved upwards, serrulate apex and fused base; about 5.0 mm wide in cupped form and 9.0 mm wide when spread, and 16.0 mm long, fused in basal 11.0 mm;

Petal color: Fused tube portion abaxial and adaxial nearest RHS 91D; upper hood petal nearest RHS 90A abaxial in the distal two-thirds with the basal one-third nearest RHS 90C, and nearest RHS 90A adaxial two-thirds and RHS 90D in basal one-third; lower labium petal outer lobes nearest RHS 90A in both abaxial and adaxial, main lobe adaxial nearest RHS 90B and abaxial variable between RHS 90D and RHS 92D along two main ridges;

Androecium: Four, two longer and two shorter vestigial; bases fused with labium, contained within hood petal;

*Filament*.—Glabrous; longer set arcuate downward along inside of upper hood, about 15.0 mm long free portion; with vestigial set protruding proximally, about 2.0 mm long, both sets less than 0.5 mm diameter; fused about 6.0 mm from base of labium petal; color region nearest RHS 91D for both sets.

*Anther*.—Glabrous, oblong, about 2.5 mm long and about 0.5 mm diameter; longitudinal, dorsifixed; color nearest RHS N92A.

*Pollen*.—Globose, less than 0.5 mm circumference; color nearest RHS 13A.

Gynoecium: One, arcuate around inside of hood petal, about 24.0 mm long and protruding in distal 4.0 mm;

*Style*.—About 22.0 mm long and about 0.7 mm diameter; color lighter than RHS NN155C at base, darkening distally to nearest RHS 90D before stigma split.

*Stigma*.—Split in two and curved in the terminal 2.0 mm; apex pointed; color nearest RHS N92D.

*Ovary*.—Superior; color nearest RHS 144A.

*Fruit*.—Nutlet, up to four at base inside calyx; rounded, about 1.0 mm diameter; color darker than RHS 200A.

Calyx: Five sepals, three upper and two lower, campanulate, apex acute; fused base; tube about 10.0 mm long and 7.0 mm tall at sepal tips and 4.0 mm wide; lower set fused to within 5.0 mm of apex and cleft about 4.0 mm deep between two lower sepals; upper set of three fused sepals to about 0.5 mm of apex;

Calyx color: Abaxial nearest RHS 137C with veins nearest RHS 137A; adaxial base nearest RHS 137D with veins nearest RHS 137B;

Bracts: Each verticil subtended by two opposite bracts; apex acuminate, base truncate, shape nearly cordate; margin minutely pubescent, and glabrous above and below; bract size up to 10.0 mm long and 8.0 mm wide, decreasing distally;

Bract color: Both surfaces nearest RHS 137A with midrib nearest RHS 145D;

Peduncles: Quadrangular in cross section; about 20 per plant; strong; mostly upright, up to 58 cm tall and 5.0 mm across at base; flowering in upper 28 cm with about 96 flowers per main stem; finely pubescent; branches upright at lower nodes with branches to about 22.0 cm long and 3.0 mm across; average distance between verticils about 15.0 mm, greater proximally and less distally;

Peduncle color: Between RHS 144A in upper and lower regions;

Pedicels: Cylindrical, about 2.0 mm long and 0.5 mm diameter; pubescent; held about 30 to 45 degrees above horizontal;

Pedicel color: Nearest RHS 145A;

Disease and pest resistance: Plants of *Salvia* 'Midnight Model' perform best with adequate moisture and good drainage; are hardy from USDA zone 3 to 8; resistant to diseases and pests beyond that common to *Salvia* has not been noted;

It is claimed:

1. The new and distinct perennial *Salvia* plant named 'Midnight Model' as herein described and illustrated useful for landscaping as a specimen plant, en masse or as a cut flower.

* * * * *